United States Patent [19]

Kreuzburg et al.

[11] 4,436,624
[45] Mar. 13, 1984

[54] CRT METHOD OF CONVERTING AND SEPARATING SUBSTANCES CONTAINED, DISSOLVED OR DISSOLVABLE IN A CARRIER LIQUID

[75] Inventors: Eberhard Kreuzburg, Mölln; Dietrich J. Von Der Pahle, Bonn; Rolf Monsheimer; Ernst Pfleiderer, both of Darmstadt; Tilman Taeger, Griesheim, all of Fed. Rep. of Germany

[73] Assignees: Universal Gesellschaft für Umwelttechnik mbH, Mölln; Röhm GmbH, Darmstadt, both of Fed. Rep. of Germany

[21] Appl. No.: 246,933

[22] Filed: Mar. 24, 1981

[30] Foreign Application Priority Data

Mar. 27, 1980 [DE] Fed. Rep. of Germany ....... 3011844

[51] Int. Cl.³ .............................................. C02F 1/24
[52] U.S. Cl. .................................... 210/632; 210/704; 210/758; 210/905
[58] Field of Search ............... 210/632, 721, 758, 905, 210/704, 705, 759, 763, 750

[56] References Cited

U.S. PATENT DOCUMENTS

| | | | |
|---|---|---|---|
| 2,020,325 | 12/1933 | Myhren et al. | |
| 3,655,343 | 4/1972 | Galeano | 210/758 X |
| 4,081,367 | 3/1978 | Hulls et al. | 210/905 X |
| 4,111,803 | 9/1978 | Townend | 210/905 X |
| 4,162,970 | 7/1979 | Zlokarnik | 210/758 X |

FOREIGN PATENT DOCUMENTS

| | | |
|---|---|---|
| 25813 | 3/1960 | European Pat. Off. |
| 1442585 | 3/1965 | Fed. Rep. of Germany |
| 1667231 | 12/1967 | Fed. Rep. of Germany |

OTHER PUBLICATIONS

Ullmanns Encyklopädie der technischen Chemie, 4., neubearbeitete und erweiterte Auflage, Band 16: "Lagerwerkstoffe Bis Milch," pp. 125–127.

Lehr-und Handbuch der Abwassertechnik, Band II (German Publication, pp. 211–212, published by Wilhelm Ernst & Son, Berlin, Munich).

Ein neues technisches Konzept: Zwei-Phasen-Pumpen Chemische Rundschau 29, (1976).

Neuer Hochleistungsfermenter nach dem Tauchstrahlverfahren Chemiker Zeitung, (1975).

*Primary Examiner*—Thomas G. Wyse
*Attorney, Agent, or Firm*—Herbert Dubno; Karl F. Ross

[57] ABSTRACT

A method and a device for converting and separating substances dissolved in a carrier fluid, more particularly proteides or proteins, by adding and mixing with an agent, e.g. enzymes, which brings about the chemical reaction or the build-up or breakdown of the molecules of the substances and causes them to precipitate. In addition these substances are mixed and come to an accelerated reaction with the agent in at least one circuit flow through a jet immersion reactor while a gas is supplied intensively thereto before froth flotation of the precipitated substances is carried out after adding means assisting flotation.

4 Claims, 1 Drawing Figure

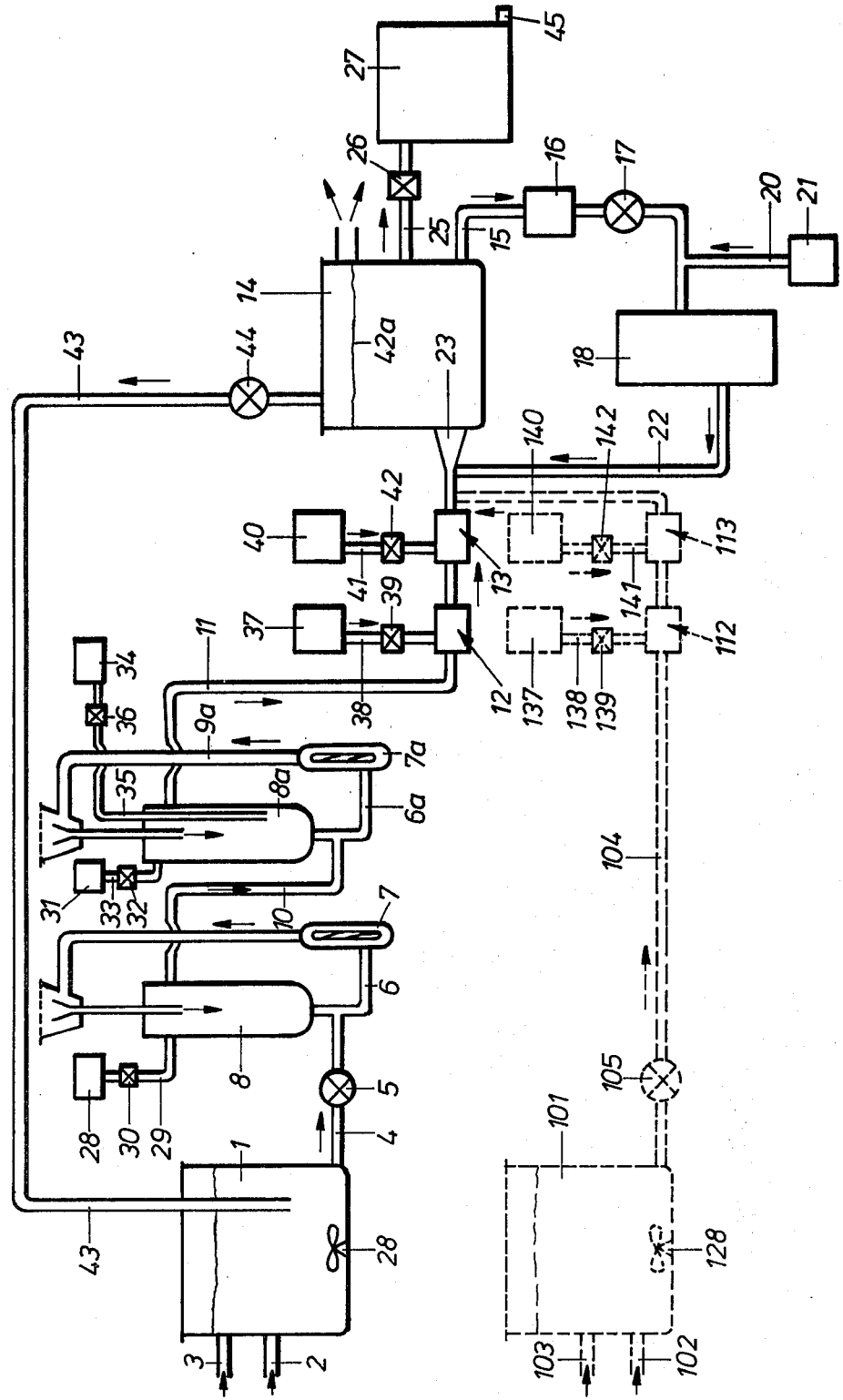

CRT METHOD OF CONVERTING AND SEPARATING SUBSTANCES CONTAINED, DISSOLVED OR DISSOLVABLE IN A CARRIER LIQUID

The invention relates to a method for converting and separating substances contained dissolved or dissolvable in a carrier liquid as for converting and separating high molecular materials dissolved in water, e.g. proteins, by chemical reaction and/or by building-up or breaking down the molecules and transferring them into a condition in which they can be precipitated out and subsequently separated.

The above mentioned method steps are known in a plurality of chemical processes for converting and separating substances contained, dissolved or dissolvable in a carrier liquid, the main area of application of these steps is in biological conversion or organic substances contained in carrier liquid.

For example, when treating effluent, the substances contained in the effluent are biologically or biochemically converted and precipitated out and separated from the effluent, for example in the form of slurry. However, damaging inorganic substances which are a nuisance to the environment may also be converted, precipitated and subsequently separated in this form.

In the method described in the introduction, it is necessary to mix the mixture which is to be treated comprising the carrier liquid and the substances contained, dissolved or dissolvable therein intensively with a gas with air or oxygen, for example, in the case of biological conversion. At the same time a chemical reaction with the inorganic substances often occurs due to the oxygen or, in addition to introducing the gas, chemical reaction substances have to be added and these also have to be mixed intensively with the mixture. In order to achieve this, it has become known to mix together or stir intensively the mixtures comprising the carrier liquid and the substances contained dissolved or dissolvable therein, the gas which has been introduced and, in some cases other substances which have been added. As a result, very different methods of mixing, stirring and supply of gas have become known, as well as the systems in which either mechanical devices are used or a flow is produced with the aid of the gas which has been introduced, said flow having one overall direction but being locally turbulent, in order to obtain very large surfaces between the gas which has been introduced and the liquid mixture so as to achieve intensive reactions. In spite of the known measures, a relatively long period of time is required, particularly in the case of biological or biochemical conversion before the substances contained in a mixture have undergone the desired conversion.

The substances precipitated or which can be precipitated out of the mixture are separated in the known methods generally by filtering or exploiting their different specific weight or by means of deposition and this separation takes a relatively long period of time.

In order to carry out the method by implementing the said method steps, a large construction cost is necessary for the required devices and/or plant.

It is the object of this invention to so design the method stated in the introduction that, while at the same time reducing the expenditure required to carry out the method, there is a considerable reduction in the time taken to carry out the method while increasing the reaction intensity and reducing the time taken for separation and achieving a particularly high degree of separation.

In order to achieve the object stated above the said method is characterised in accordance with the invention by the fact that the mixture, for chemically converting and/or building-up or breaking-down the molecules of the substance contained in the liquid and for transferring the substance into a precipitated condition or a condition in which it can be precipitated while adding an agent, which causes conversion and/or build-up or breakdown of the molecules, in metered amounts, is passed through at least one jet immersion reactor operating like a jet pump and through a subsequent two phase pump and is acted upon by a gas in the jet immersion reactor and subjected to froth flotation after the precipitated substance has been separated.

In order to carry out the biochemical processes for example for the manufacture of yeasts or other biochemical substances, it is known to use jet immersion reactors in conjunction with a two phase pump arranged thereafter so as to pass the material which is to be treated several times through the jet immersion reactor while at the same time supplying gas, generally air or oxygen, and in this way to achieve a build-up of the molecules in a carrier liquid which is necessary in order to produce the yeasts or some other biological substance. On the other hand the use of the jet immersion process as an initial stage in the separation of a substance contained, dissolved or dissolvable in a carrier liquid, more particularly in conjunction with the breakdown of the molecules of the said substance is not known and, in conjunction with the subsequent separating process by froth flotation of the precipitated substance, is not only new but has a surprising effect. The relatively long period of treatment of the mixture comprising the carrier liquid and the substance dissolved or dissolvable therein, which was required previously, can be dispensed with and, particularly in the case of biological reactions, as well as reducing the duration of the reaction processes there is an intensive and complete reaction due to the spatially and temporily, largely homogeneous course of the processes. In addition the froth flotation, which is known per se and is used as a second method step in conjunction with the jet immersion process, provides an exceptionally favorable result from separation for the separation process itself over a small period of time. The method can be implemented either in batches or continuously.

The new method is suitable for very different conversion and separation processes in which the supply of a gas, more particularly air or oxygen, is required for conversion. Depending on the mixture which is to be separated, the expert is able to select the required agents for achieving the substances which are precipitated or can be precipitated based on his technical expertise. This can be done in known metered amounts during the immersion jet process or during precipitation immediately before froth flotation while supplying the mixture which is being treated preliminarily and which has been passed out of the jet immersion reactor into the froth flotation device.

More particularly, in order to separate large molecular materials dissolved in water e.g. proteins, the new method is suitable and has already proved its worth in practice. However, it is also possible, using the method described, to separate sulphides, for example, from a mixture of water and other substances by means of catalytic oxidation, e.g. by conversion of the sulphide into sulphate in the presence of calcium ions in order to obtain $CaSo_4$.

It has also proved to be particularly advantageous to pass the mixture through the jet immersion reactor while adding enzymes and therefore to mix it with air or oxygen for the purpose of biologically converting and separating proteins from water which forms the carrier liquid, in effluent for example.

It is known that proteins in a carrier liquid can be broken down until their respective molecular chains have reached a certain length. This process is only completed however when air or oxygen is added, so that intensive stirring or mixing is advantageous while at the same time treating the enzymes in a manner so as to preserve them. This is achieved by treating the mixture provided with the enzymes for a short time in the jet immersion reactor while at the same time homogenizing the entire mixture. By adding flocking and precipitation means at the same time, the proteins which have been broken down with respect to their molecular chains may be precipitated in the jet immersion reactor so as to separate them almost completely from the carrier liquid in the subsequent froth flotation process and supply them to a further dressing plant or further processing plant.

According to another feature of the invention it is also possible, by homogenizing the mixture subjected to the jet immersion process to a large extent, which is achieved during the said jet immersion process, to produce a mixture comprising the carrier liquid and proteins in the jet immersion reactor only when the enzymes are added at the same time, or to enrich the mixture with proteins and to implement conversion of the proteins in the jet immersion reactor i.e., by breaking down the molecules. The above mentioned feature is of particular interest in cases where a concentrate of proteins is obtained for example from treating a material in the preliminary process, the said proteins not being able to be processed any further in the form in which they are obtained so that it is necessary for them to be converted. In these cases, the mixture comprising the carrier liquid and the proteins may be manufactured only in the jet immersion reactor or if proteins are already contained in the liquid passed through the jet immersion reactor, then the liquid may be concentrated while at the same time the substances are broken down by the enzymes which have been supplied.

The above mentioned difficulties may arise when processing meat or fish products for example in which, as experience has shown, effluent or mixtures of water and other substances with a very high proportion of proteins are obtained and also other effluent which only has very small proportions of these substances.

In most cases, the mixtures which are to be treated are effluent containing inorganic substances as well as organic substances. In order to treat this effluent the invention provides for multiple treatments, by passing the effluent through the jet immersion reactor or jet immersion reactors, and by carrying out in the first stage a chemical reaction, such as oxidation of inorganic substances which are a nuisance to the environment and in the second stage conversion of the organic substances contained in this liquid more particularly the proteins and transfer into a precipitated condition. The organic and inorganic substances may be separated jointly by froth flotation and the substances separated from the carrier liquid during froth flotation are subsequently dressed into individual components. This separation can generally be carried out without any great expense.

A particular field of application of this multiple treatment stated above is for effluent from tanneries containing sulphides and proteins. This effluent may be treated in the following manner:

A catalytic oxidation of the sulphide with $MnSO_4$ for example, takes place in a first stage and in the second stage the proteides or proteins are converted by adding enzymes and by transferring them into a condition in which they can be precipitated. After the first treatment stage, the machine scrapings and collagen and keratin residues may be added in finely chopped form to the effluent, the scrapings and residues being obtained during the manufacture of leather. In this way, the proteins are extracted from the effluent obtained in the tanneries in a form in which they can be used subsequently, while at the same time overcoming the sulphide problem and at the same time converting the machine scrapings and the collagen and keratin residues which can hardly be used in the form in which they are originally obtained or can only be used with difficulty. Therefore, it is possible to separate and extract the fats at the same time by using the method and these fats are separated out of the effluent together with the proteins and can be used separately by dressing the separated substances.

Devices for carrying out the method may be so formed that at least one jet immersion reactor known by the name fermenter and having a two phase pump is connected at the inlet side to a collector for the mixture which is to be treated and at the outlet side to a flotation container in which the supply line from the jet immersion reactor to the flotation container is equipped with devices for metered supply of a flocking and precipitation means and is connected to a further device for introducing a liquid/gas mixture which is at high pressure. In this device, the substances which are to be separated from the mixture are only flocked and precipitated while the mixture which has previously been treated in the fermenter or fermenters is transferred, although the precipitation and flocking agents could also be added in the fermenters. The supply of this precipitation and flocking means into the connection line between the fermenter and the flotation container does have the advantage however that any changes in metering with regard to the means added can be detected more rapidly because of the flotation which follows on immediately therefrom and metering is also more sensitive to the result of flotation. It is particularly advantageous if a by-pass line connecting the flotation container to the inflow line is provided for introducing the liquid/gas mixture which is at high pressure, in which by-pass line a high pressure pump and a regenerative boiler are arranged, and a compressed air line opens into the line between the pump and the boiler and has a controllable compressed air source connected to it. The introduction of the liquid/gas mixture which has been mentioned above, leads, according to experience, to extremely fine gas bubbles while at the same time distributing the gas bubbles over the whole of the flow cross section and the gas bubbles are formed in a pressure release region which is funnel-shaped for example and releases the pressure in the supply line to the flotation container.

The drawing shows the arrangement and the formation of a device carrying out the method in schematic view such as can be used to treat effluent from tanneries while at the same time processing the machine scrapings.

In the embodiment shown in the drawings, it is assumed that the effluent present in the tanneries is separated after those occurring when washing the skins and coats, of the animals before they are subjected to further processing. This effluent, which is also called washing liquor, may be treated in the usual way by biologically breaking it down, for example in appropriate pools with aeration devices and it may then be discharged into the usual channel system.

The effluent obtained during the subsequent treatment of the skins and coats is separated into chromium free effluent and effluent which contains chromium. These two types of effluent are also obtained in different stages of treatment of the leather so that separation often does not create any great difficulty.

In the drawings, it is assumed that the alkaline effluent from a tanner is subjected to the process provided in accordance with the invention, in the arrangement shown by the continuous line. This is lime liquor obtained in the tanneries which is subjected to the method described at the outset in accordance with the comments below using the arrangement shown in the drawings together with the leather machine scrapings, or leather scrapings for short, in order to separate from the lime liquor and the scrapings those substances which may subsequently be further processed usefully without any great expense.

In the drawings, the respective flow directions are shown by individual lines by arrows for the sake of simplicity.

The arrangements shown in solid lines comprise a collecting container 1 to which the alkaline effluent of a tannery is supplied through supply connections 2 and 3. A line 4 with a pump arranged therein leads from the collecting container 1 to a connection line 6 to the suction side of a two phase pump 7, the two phase pump 7 cooperating with a first jet immersion reactor 8. The jet immersion reactor 8 is known in its construction from fermentation techniques so that closer description of this reactor is not necessary. The jet immersion reactor 8 is connected at its lower end via the line 6 to the suction side and via the line 9 to the compression side of the two-phase pump so that the pump 7 and the jet immersion reactor 8 cause the mixture passed through this jet immersion reactor to be conveyed along the circuit.

A second jet immersion reactor 8a with an associated further two phase pump 7a is connected to the jet immersion reactor 8 via a connection line 10. The line 10 leads into the suction line 6a of the pump 7a which in turn is connected in the same way via the line 9a on the compression side to the jet immersion reaction 8a as has already been described in conjunction with jet immersion reactor 8 and the line 9 as well as the two phase pump 7.

A connection line 11 leads from the jet immersion reactor 8a via a first metering device 12 and a second metering device 13 to a flotation container 14.

The flotation container 14 has a device for introducing a liquid/gas mixture which is at high pressure. This device comprises a suction line connected to the flotation container 14, which suction line 15 opens into an intermediate container 16 to which is connected a high pressure pump 17 via a connection line, the said high pressure pump 17 being connected at the outlet side via a connection line 19 to a storage (regenerative) boiler 18. The line 19 between the high pressure pump and the regenerative boiler 18 is connected to a compressed gas line 20 which in turn is connected to a compressed air generator 21. A connection line 22 leads from the regenerative boiler 18 to the supply line 11 and in fact to a point which is directly in front of the opening of this supply line into the flotation container 14. The portion between the opening of the line 22 into the line 11 and the flotation container 14 is formed as a funnel shaped portion 23. As a result the gas introduced through the liner 22 at very high pressure into the flotation container 14 with the liquids supplied forms very small bubbles which, as is known, are favourable for froth flotation.

An outlet connection 24 is connected to the upper part of the flotation container 14, while a further collector 27 is connected to the lower part of the flotation container 14 via a line 25 with a valve 26 arranged therein.

The mode of operation of the device described previously is as follows:

The chrome free effluent from the tannery is passed into the collector 1 which is equipped with a stirring element 28 designed to distribute the materials contained in the effluent uniformly. This alkaline effluent contains a considerable quantity of proteins such as keratins, collagens and fats. The effluent is supplied out of the collecting container 1 to the two phase pump 7 with the aid of a pump 5 in metered quantities and the two phase pump 7 conveys the effluent through the jet immersion reactor 8 producing the flow which has already been mentioned. In the example shown, a proportion of the effluent treated in the jet immersion reactor is drawn out of this flow through the line 10 and passed to the second jet immersion reactor 8a. Instead of this, a valve may be arranged in the line 10 so that the effluent introduced into the jet immersion reactor 8 may be treated in batches.

The effluent may be mixed intensively with air from the atmosphere in the jet immersion reactor 8 and this air may be entrained during operation of the jet immersion reactor and mixed intensively with the effluent due to the action of the immersion jet.

Initially the sulphide contained in the alkaline effluent from the tannery is catalytically oxidized in the first jet immersion reactor 8. To this end $MnSO_4$ is supplied to the effluent which is passed through the jet immersion reactor 8 in a circuit from the supply container 28 and via a supply pipe 29 with a metering valve 30. The resultant sulphate, in the presence of calcium ions which are already present in the effluent, leads to precipitation of $CaSO_4$ so that the salt content of the effluent is reduced at the same time. The known sulphite-/sulphate corrosion to which concrete construction are particularly vulnerable is reduced at the same time.

The effluent treated in the jet immersion reactor 8 is supplied in the manner described, either continuously or in batches, to the second jet immersion reactor 8a in which the proteins are dressed or converted and entrained in the effluent or added to the effluent in this treatment stage while the effluent treated in the jet immersion reactor 8a is mixed with substances containing proteins more particularly scrapings obtained in the tannery.

In order to achieve the breakdown of the long-chain molecules of the proteides or proteins, enzymes are supplied to the effluent in the jet immersion reactor 8a, for example, an alkaline bacteria proteinase. A supply container 31 with a substance containing the enzymes, a metering device 32 and a supply line 33 connected to the jet immersion reactor 8 serve to supply the enzymes. Furthermore, the leather scrapings obtained when processing the leather and the residues of collagen and keratin are supplied in metered form with a metering valve 36 from a container 34 and through a supply line 35 to the jet immersion reactor 8a, the said residues having been crushed as finely as possible beforehand.

Due to the very intensive mixing of the effluent, which has been enriched with the protein-containing materials, with oxygen from the air, the long-chain molecules of the proteins are broken down biologically in the jet immersion reactor 8a while at the same time hydrolysing the scrapings supplied and the said residues of collagen and keratin. This breakdown is achieved largely due to the enzymes used in conjunction with the oxygen, breakdown can be carried out in controlled manner depending on the type and quantity of enzyme used. The effluent or the proteins contained in the effluent or supplied thereto are conditioned in the jet immersion reactor 8a so that they are obtained in a composition which is favourable for further processing for example for fodder or for further processing in the food industry during subsequent froth flotation.

The mixture treated in the jet immersion reactor 8a is mixed initially with a means assisting flocking (flocking catalyst) for example a substance having multivalent metal cations or a plyacrylic acid derivative while being transported along the line 11 to the flotation container 14 via the metering device 12. This auxiliary flocking agent is supplied out of the supply container 37 via the line 38 and a metering valve 39. In the metering device 13 which is arranged thereafter a precipitating agent, for example $H_2SO_4$, is supplied to the flow of material flowing into the flotation container out of a supply container 40 via the line 41 and a metering valve 42.

In the manner described above adding the liquid under high pressure and containing the gas brings about froth flotation which is completed in the flotation container 14 so that the substances to be separated from the effluent collect on the surface 42a of the flotation container 14 in the form of foam and are removed via the connection 24 and subjected to subsequent dressing, indicated by the arrow, for example to sub-division into proteins and fats.

The means assisting flocking or the precipitation means could also be added in the jet immersion reactor 8a so that the substances to be separated are not transferred into a condition in which they can be precipitated in this reactor but go straight there for precipitation so as to be extracted by the foam flotation device arranged thereafter.

A return line 43 from the flotation container 14 is provided with a pump 44 in accordance with the drawings through which $H_2S$ is drawn by suction and passed back into the collecting container 1.

The arrangement described in conjunction with the treatment of alkaline tannery waters is suitable in its basic construction for treating other effluent too, for example, effluent from the meat or fish industry in which the respective agents have to be adapted accordingly to the substances contained in the effluent. In addition it is quite possible to use only one jet immersion reactor instead of the two jet immersion reactors 8 and 8a described in the example in which the sought after reactions or conversions take place.

In the example of treatment of alkaline effluent from tanneries, shown in the drawings and described above, the plants in accordance with the broken line representation may be combined with dressing effluent containing chromium, which is obtained in an acidic form. In order to do this a collecting container 101 may be provided which is fed via supply lines 102 and 103 and is equipped with an agitator 128. This collecting container 101 is connected via a line 104 to a pump 105 in which metering devices 112 and 113 are provided along the line 104. In addition with the aid of the metering device 112 a flotation assisting means, e.g. polyamid-chromide is introduced out of the container 137 via a line 138 and a metering valve 139 into the line 104 while the other metering device 113 serves to supply a lye. A supply container 140 with a supply line 141 and a metering valve 142 arranged in this line is provided for this purpose. The acidic effluent mixed with the flotation assisting means and with the lye, the said effluent coming from the collecting container 101, is subjected to flotation together with the alkaline effluent from the collecting container 1. Combining the two effluents results in substantial neutralization in the flotation container 14.

The effluent arriving in the collecting container 27 from the flotation container 14 via the line 25 and valve 26 and released by the proteins and fats is neutralized in this container and passed for biological re-treatment through a connection 45 for example a main canal.

Data for treating alkaline tannery effluent such as may be treated in the manner as described above with the aid of the devices shown in the drawings is given below by way of example.

The following is line liquor with approximately the following composition.
(a) pH value 10–12
(b) keratinous protein material of hair and epidermis
(c) sulphides up to 2000 mg/l
(d) Fats, tensides and lime soaps The $BSB_5$ value is approximately 1000 mg $O_2$/l the CSB value is approximately 20000 mg $O_2$/l.

Approximately 50 to 80 g $MnSO_4/m^3$ is added to the sulphate oxidation in the first jet immersion reactor while a residence time of approximately 30 minutes is set during treatment in this jet immersion reactor.

In the second jet immersion reactor approximately 15 to 20 kg of machine parings per $m^3$ is added. Furthermore approximately 40 g of enzymes per $m^3$ is added in the form of an alkaline bacteria proteinase. The residence time is also approximately 30 minutes during treatment in the second immersion current reactor.

Approximately 0.01% of means assisting flocking ((flocking catalyst)) is supplied via the first metering device. $H_2SO_4$ is supplied with the second metering device in such a quantity that a pH value of 3.5 is produced.

Because of the setting of the pH value mentioned above the rest of the sulphate is driven off during froth flotation as $H_2S$ and is passed back into the collecting container 1 in the manner described. The natural fats are also separated off with the proteins during flotation. Among others $CaSO_4$ and CaO and other non-soluble products are obtained as bottom settlings in the form of a slurry which is low in water content and disposable.

The effluent treated in this way is largely sulphide-free and in the case of $BSB_5$ has a maximum of 15% of its starting value and substantially lower CSB values and is almost free of fats.

The chromium salts are precipitated and floated as alkaline hydroxides with a pH of 11 to 12 during treatment of the chromium-containing effluent in the manner described, as a result of which the chromium can be regained from the separated substances. The chromium hydroxide can be extracted as $Cr(OH)_3$ and can be replaced again, dissolved in $H_2SO_4$.

We claim:

1. A method of recovering a high molecular weight material from water containing a dissolved proteinaceous substance, said method comprising the steps of:
   (a) circulating the water containing said substance through a first jet immersion reactor in which the water containing the substance is forced through a small cross-section passage into a vessel containing the water and the substance, and of larger cross section, the circulation being effected with a two-phase pump having a suction side connected to said vessel and a discharge side connected to said passage, thereby breaking down molecules of said substance;
   (b) passing water from said vessel containing said substance in a dissolved and broken-down state into a second two-phase pump and circulating it through a second jet immersion reactor having a respective passage communicating with the discharge side of said second pump and opening into a vessel of larger cross section containing liquid and communicating with the suction side of said second pump, thereby causing the frothing of the broken-down substance in said liquid;
   (c) adding enzymes to at least one of said reactors for promoting the breakdown of said substance therein;
   (d) adding a flocculating agent to at least said second reactor for promoting the separation of broken-down substances from said liquid; and
   (e) separating the broken-down substance from the liquid of said second reaction by flotation.

2. The method defined in claim 1, further comprising mixing oxygen with the circulated water and substance in at least one of said reactors by an entrainment of the oxygen to the respective passage.

3. The method defined in claim 2 wherein the water containing said substance is an effluent from a tannery containing sulfides, further comprising the step of catalytically oxidizing the sulfides in the first reactor with permanganate, said substance being added in said second reactor.

4. The method defined in claim 3 wherein collagen and keratin residues are added in finely divided form to the liquid of said second reactor.

* * * * *